United States Patent [19]
Dinsmore

[11] Patent Number: 5,837,236
[45] Date of Patent: Nov. 17, 1998

[54] ISOLATED PORCINE PANCREATIC CELLS FOR USE IN TREATMENT OF DISEASES CHARACTERIZED BY INSUFFICIENT INSULIN ACTIVITY

[75] Inventor: Jonathan Dinsmore, Brookline, Mass.

[73] Assignee: Diacrin, Inc., Charlestown, Mass.

[21] Appl. No.: 784,098

[22] Filed: Jan. 15, 1997

Related U.S. Application Data

[62] Division of Ser. No. 327,506, Oct. 21, 1994, Pat. No. 5,629,194.

[51] Int. Cl.$^6$ .............................. A01N 63/00; C12N 5/00
[52] U.S. Cl. ............................................ 424/93.7; 435/325
[58] Field of Search ........................... 514/866; 424/93.7; 435/325; 436/548

[56] References Cited

FOREIGN PATENT DOCUMENTS

| | | | |
|---|---|---|---|
| 0 191 613 | 8/1986 | European Pat. Off. ........ | A61K 35/39 |
| WO 92/04033 | 3/1992 | WIPO ............................. | A61K 35/00 |
| WO 92/09688 | 6/1992 | WIPO ............................. | C12N 15/00 |
| WO 93/02188 | 2/1993 | WIPO ............................. | C12N 15/00 |
| WO 95/26741 | 10/1995 | WIPO ............................. | A61K 35/39 |

OTHER PUBLICATIONS

Alumets, J. et al., "Ontogeny of Endocrine Cells in Porcine Gut and Pancreas," *Gastroenterology*, vol. 85, No. 6, pp. 1359–1372, Dec. 1983.

Andersson, A., "Synthesis of DNA in Isolated Pancreatic Islets Maintained in Tissue Culture," *Endocrinology*, vol. 96, No. 4, pp. 1051–1054, 1975.

Andersson, A. et al., "Transplantation of Porcine Fetal Islet–Like Cell Clusters to Three Diabetic Patients," *Transplantation Proceedings*, vol. 24, No. 2, pp. 677–678, 1992.

Bjöersdorff, A. et al., "Microbiologic Screening As A Preparatory Step For Clinical Xenografting of Porcine Fetal Islet–Like Cell Clusters," *Transplantation Proceedings*, vol. 24, No. 2, pp. 674–676, 1992.

Brelje, T.C. and R.L. Sorenson, "Role of Prolactin Versus Growth Hormone on Islet B–Cell Proliferation in Vitro: Implications for Pregnancy," *Endocrinology*, vol. 128, No. 1, pp. 45–57, 1991.

Chatterjee, A.K. et al., "Epidermal Growth Factor Stimulates (Pro–) Insulin Biosynthesis and $^3$H–Thymidine Incorporation in Isolated Pancreatic Rat Islets," *Horm. metabol. Res.*, vol. 18, No. 1, pp. 873–874, 1986.

Dinsmore, J.H. and J. Ratliff, "Isolation, Growth, Differentiation, and Transplantation of Pig Fetal Pancreatic Cells," *Molecular Biology of the Cell*, Supp. 5, 350A (Abstract No. 2032), 1994.

Dreval, A.V. et al., "Parameters of the Immune Status in Patients With Newly Diagnosed Type 1 Diabetes Mellitus After Islet Cell Transplantation," *Transplantation Proceedings*, vol. 24, No. 6, pp. 3041–3042, Dec. 1992.

Faustman, D. and C. Coe, "Prevention of Xenograft Rejection by Masking Donor HLA Class I Antigens," *Science*, vol. 252, pp. 1700–1702, 1991.

Faustman, D. and C. Coe, "Xenograft Acceptance by Masking Donor Antigens," *Transplantation Proceedings*, vol. 24, No. 6, pp. 2854–2855, Dec. 1992.

Faustman, D.L. et al., "Prevention of Rejection of Murine Islet Allografts by Pretreatment with Anti–Dendritic Cell Antibody," *Proc. Natl. Acad. Sci. USA*, vol. 81, pp. 3864–3868, Jun. 1984.

Groth, C.G. et al., "Evidence of Xenograft Function In a Diabetic Patient Grafted With Porcine Fetal Pancreas," *Transplantation Proceedings*, vol. 24, No. 3, pp. 972–973, Jun. 1992.

Groth, C.G. et al., "Transplantation of Porcine Fetal Islet–Like Cell Clusters Into Eight Diabetic Patients," *Transplantation Proceedings*, vol. 25, No. 1, p. 970, 1993.

Hellerström, C. et al, "Method for Large–Scale Isolation of Pancreatic Islets by Tissue Culture of Fetal Rat Pancreas," *Diabetes*, vol. 28, pp. 769–776, Aug. 1979.

Holgersson, J. et al., "Carbohydrate Specificity of Human Immunoglobulin–M Antibodies With Pig Lymphocytotoxic Activity," *Transplantation Proceedings*, vol. 24, no. 2, pp. 605–608, Apr. 1992.

Kaiser, N. et al., "Monolayer Culture of Adult Rat Pancreatic Islets on Extracellular Matrix; Long Term Maintenance of Differentiated B–Cell Function," *Endocrinology*, vol. 123, No. 2, pp. 834–840, 1988.

Korsgren, O. et al., "Effects of Culture Conditions on Formation and Hormone Content of Fetal Porcine Isletlike Cell Clusters," *Diabetes*, vol. 38, Suppl. 1, pp. 209–212, Jan. 1989.

Korsgren, O. et al., "Functional and morphological differentiation of fetal porcine islet–like cell clusters after transplantation into nude mice," *Diabetologia*, vol. 34, pp. 379–386, Spring 1991.

(List continued on next page.)

Primary Examiner—Sandy Saucier
Attorney, Agent, or Firm—Jean M. Silveri; Lahive & Cockfield, LLP

[57] ABSTRACT

Isolated porcine pancreatic cells, isolated populations of such cells and methods for isolating and using the cells to treat subjects with diseases characterized by insufficient insulin activity are described. The porcine pancreatic cells are preferably non-insulin-secreting porcine pancreatic cell having the ability to differentiate into an insulin-secreting cell upon introduction into a xenogeneic subject, such as a human subject. Such cells include embryonic porcine pancreatic cells obtained from embryonic pigs between about day 31 and day 35 of gestation. The porcine pancreatic cells can be modified to be suitable for transplantation into a xenogeneic subject, for example, by altering an antigen (e.g., an MHC class I antigen) on the cell surface which is capable of stimulating an immune response against the cell in the subject (e.g., by contact with an anti-MHC class I antibody, or a fragment or derivative thereof). The isolated porcine pancreatic cells of the invention can be used to treat diseases characterized by insufficient insulin activity, e.g., Type I and Type II diabetes, by administering the cells to a subject having such a disease.

35 Claims, 2 Drawing Sheets

OTHER PUBLICATIONS

Korsgren, O. et al., "Large–Scale Production of Fetal Porcine Pancreatic Isletlike Cell Clusters," *Transplantation*, vol. 45, No. 3, pp. 509–514, Mar. 1988.

Korsgren, O. et al., "Pretreatment of fetal porcine pancreas in culture with nicotinamide accelerates reversal of diabetes after transplantation to nude mice," *Surgery*, vol. 113, pp. 205–214, 1993.

Kumagai–Braesch, M. et al., "Immune Response of Diabetic Patients Against Transplanted Porcine Fetal Islet Cells," *Transplantation Proceedings*, vol. 24, No. 2, pp. 679–680, Apr. 1992.

Lacy, P.E. et al., "Prolongation of Islet Allograft Survival Following in vitro Culture (24° C.) and a Single Injection of ALS," *Science*, vol. 204, pp. 312–313, 1979.

Liu, X. et al., "Persistent Reversal of Diabetes by Transplantion of Fetal Pig Proislets Into Nude Mice," *Diabetes*, vol. 40, pp. 858–866, 1991.

Löhr, J.M. and M.B.A. Oldstone, "Detection of Cytomegalovirus Nucleic Acid Sequences in Pancreas in Type 2 Diabetes," *The Lancet*, vol. 336, No. 8716, pp. 644–648, 1990.

Markmann, J.F. et al., "Indefinite Survival of MHC Class I–Deficient Murine Pancreatic Islet Allografts," *Transplantation*, vol. 54, No. 6, pp. 1085–1089, 1992.

Montesano, R. et al., "Collagen Matrix Promotes Reorganization of Pancreatic Endocrine Cell Monolayers into Islet–like Organoids," *Journal of Cell Biology*, vol. 97, pp. 935–939, Sep. 1983.

Munn, S.R. and C. Marjoribanks, "Abrogation of Islet Immunogenicity Using an Anti–MHC Class I Monoclonal Antibody," *Transplantation Proceedings*, vol. 24, No. 3, pp. 1038–1039, Jun. 1992.

Munn, S.R. and C. Marjoribanks, "Masking Donor Histocompatibility Complex Class I Antigens on Allogeneic Islets," *Transplantation Proceedings*, vol. 24, No. 6, p. 2857, Dec. 1992.

Nielsen, J.H., "Effects of Growth Hormone, Prolactin, and Placental Lactogen on Insulin Content and Release, and Deoxyribonucleic Acid Synthesis in Cultured Pancreatic Islets," *Endocrinology*, vol. 110, No. 2, pp. 600–606, 1982.

Nielsen, J.H., "Growth Hormone is a Growth Factor for the Differentiated Pancreatic β–Cell," *Molecular Endocrinology*, vol. 3, No. 1, pp. 165–173, 1989.

Osorio, R.W. et al., "Prolongation of in vivo Mouse Islet Allograft Survival by Modulation of MHC Class I Antigen," *Transplantation*, vol. 57, No. 6, pp. 783–788, 1994.

Otonkoski, T. et al., "Nicotinamide Is a Potent Inducer of Endocrine Differentiation in Cultured Human Fetal Pancreatic Cells," *J. Clin. Invest.*, vol. 92, pp. 1459–1466, 1993.

Pittman, K. et al., "Use of Discordant Islet Xenografts for the Treatment of Type II Diabetes," *Transplantation Proceedings*, vol. 26, No. 3, pp. 1135–1137, Jun. 1994.

Pyzdrowski, K.L. et al., "Preserved Insulin Secretion and Insulin Independence in Recipients of Islet Autografts," *New England Journal of Medicine*, vol. 327, No. 4, pp. 220–226, 23 Jul. 1992.

Rabinovitch, A. et al., "Growth Hormone Stimulates Islet B–Cell Replication in Neonatal Rat Pancreatic Monolayer Cultures," *Diabetes*, vol. 32, pp. 307–312, Apr. 1983.

Roark, J.H. et al., "Prolongation of Rat Pancreatic Islet Allograft Survival by Anti–$CD_2$ Monoclonal Antibody Treatment," *Transplantation*, vol. 54, No. 6, pp. 1098–1103, 1992.

Rosengard, B.R. et al., "Induction of Specific Tolerance to Class I–Disparate Renal Allografts in Miniature Swine With Cyclosporine," *Transplantation*, vol. 54, No. 3, pp. 490–497, Sep. 1992.

Sasaki, N. et al., "Fetal Pancreas Transplantation in Miniature Swine," *Transplantation*, vol. 38, No. 4, pp. 335–340, 1984.

Satake, M. et al., "Kinetics and Character of Xenoantibody Formation in Diabetic Patients Transplated with Fetal Porcine Islet Cell Clusters," *Xenotransplantation*, vol. 1, pp. 24–35, 1994.

Shishko, P.I. et al., "Islet Cell Transplantation in Induction and Prolongation of Insulin–Dependent Diabetes Remission," *Transplantation Proceedings*, vol. 24, No. 6, p. 3040, Dec. 1992.

Simeonovic, C.J. and K.J. Lafferty, "The Isolation and Transplantation of Foetal Mouse Proislets," *Aust. J. Exp. Biol. Med. Sci.*, vol. 60, Pt. 4, pp. 383–390, 1982.

Simeonovic, C.J. et al., "Antibody–Induced Rejection of Pig Proislet Xenografts in $CD4^+$ T Cell–Depleted Diabetic Mice," *Transplantation*, vol. 50, No. 4, pp. 657–662, Oct. 1990.

Simeonovic, C.J. et al., "Effect of GK1.5 Monoclonal Antibody Dosage on Survival of Pig Proislet Xenografts in $CD4^+$ Cell–Depleted Mice," *Transplantation*, vol. 49, No. 5, pp. 849–856, May 1990.

Soon–Shiong, P. et al, "Long–term Reversal of Diabetes by the Injection of Immunoprotected Islets," *Proc. Natl. Acad. Sci. USA*, vol. 90, pp. 5843–5847, Jun. 1993.

Sorenson, R.L. et al., "Prolactin (in Vitro) Decreases the Glucose Stimulation Threshold, Enhances Insulin Secretion, and Increases Dye Coupling among Islet B Cells," *Endocrinology*, vol. 121, No. 4, pp. 1447–1453, 1987.

Steele, D. et al., "Transplantation of Pancreatic Islets in Diabetic Nonhuman Primates," *Transplantation Proceedings*, vol. 26, No. 6, pp. 3317–3318, 1994.

Stock, P.G. et al., "Modulation of MHC Class I Antigen Decreases Pancreatic Islet Immunogenicity," *Journal of Surgical Research*, vol. 46, No. 4, pp. 317–321, Apr. 1989.

Swenne, I., "The Role of Glucose in the In Vitro Regulation of Cell Cycle Kinetics and Proliferation of Fetal Pancreatic B–Cells," *Diabetes*, vol. 31, pp. 754–760, Sep. 1982.

Swenne, I. et al., "Effects of Platelet–Derived Growth Factor and Somatomedin–C/Insulin–Like Growth Factor I on the Deoxyribonucleic Acid Replication of Fetal Rat Islets of Langerhans in Tissue Culture," *Endocrinology*, vol. 122, No. 1, pp. 214–218, 1988.

Thivolet, C.H. et al., "Morphological and Functional Effects of Extracellular Matrix on Pancreatic Islet Cell Cultures," *Experimental Cell Research*, vol. 159, pp. 313–322, 1985.

Thompson, S.C. and T.E. Mandel, "Fetal Pig Pancreas," *Transplantation*, vol. 49, No. 3, pp. 571–581, Mar. 1990.

Tsunoda, T. et al., "Functional Maturation of Porcine Fetal Pancreatic Explants," *Transplantation Proceedings*, vol. 21, No. 1, pp. 2667–2668, 1989.

Wahoff, D.C. et al., "Intraperitoneal Transplantation of Microencapsulated Canine Islet Allografts With Short–Term, Low–Dose Cyclosporine for Treatment of Pancreatectomy–Induced Diabetes in Dogs," *Transplantation Proceedings*, vol. 26, No. 2, p. 804, Apr. 1994.

Whittaker, P.G. and K.W. Taylor, "Direct Effects of Rat Growth Hormone on Rat Islets of Langerhans in Tissue Culture," *Diabetologia*, vol. 18, pp. 323–328, Spring 1980.

Wilson, J.D. et al., "Role of CD4+ T–Lymphocytes in Rejection by Mice of Fetal Pig Proislet Xenografts," *Diabetes,* vol. 38 (Suppl. 1), pp. 217–219, 1989.

Yoneda, K. et al., "Fetal Pancreas Transplantation in Miniature Swine, II. Survival of Fetal Pig Pancreas Allografts Cultured at Room Temperature," *Diabetes,* vol. 38 (Suppl. 1), pp. 213–216, Jan. 1989.

ISOLATED PORCINE PANCREATIC CELLS FOR USE IN TREATMENT OF DISEASES CHARACTERIZED BY INSUFFICIENT INSULIN ACTIVITY

This application is a divisional application of Ser. No. 08/327,506 filed on Oct. 21, 1994, now U.S. Pat. No. 5,629,194. The contents of all of the aforementioned application are hereby incorporated by reference.

BACKGROUND OF THE INVENTION

Idiopathic or primary diabetes mellitus is a chronic disorder of carbohydrate, fat, and protein metabolism characterized in its fully expressed form by an absolute or relative insulin deficiency, fasting hyperglycemia, glycosuria, and a striking tendency toward development of atherosclerosis, microangiopathy, nephropathy, and neuropathy. Underutilization of glucose is characteristic of all diabetic patients, but only some have a clearly defined severe insulin deficiency resulting from a loss of $\beta$ cells. The large remainder of diabetic patients suffer from some impairment of insulin secretory response associated with a marked resistance to insulin in the peripheral tissues.

The phrase "idiopathic diabetes mellitus" embraces a heterogeneous group of disorders having in common the above-described characteristics. At least two major as well as several less common variants of the disease have been identified. One major variant, insulin-dependent diabetes mellitus (IDDM) (Type I), accounts for about 10% of diabetics. A second major variant, non-insulin-dependent diabetes mellitus (NIDDM) (Type II) represents the remaining 90% of all diabetic patients. Robbins, S. L. et al. Pathologic Basis of Disease, 3rd Edition (W. B. Saunders Company, Philadelphia, 1984) p. 972. Absent regular insulin replacement therapy using exogenously produced insulin and/or careful monitoring of the diet of diabetic patients, such patients experience a wide range of debilitating symptoms, some of which can progress into coma and ultimately death.

An alternative method of treating diabetes presently under investigation, which does not require repeated administration of insulin and/or strict monitoring of diet, is transplantation of pancreatic cells or tissue from a donor to the diabetic patient. A major problem in pancreatic cell or tissue transplantation from one human to another for treatment of diabetes, however, is a shortage of donor tissue. Thompson, S. C. et al. (1990) Transplantation 49(3):571–581. Moreover, human pancreas will inevitably remain in limited supply and be subject to many constraints, including, especially with human fetal pancreatic cells or tissue, sensitive ethical issues. The improvement in patients and graft survival following human pancreas transplants (Sutherland, D. E. R. et al. (1987) Transplant. Proc. 19:113) will also mean that adult cadaveric pancreas may be more difficult to obtain for experimental purposes.

As a result of the above-described problems associated with transplantation of pancreatic tissue from a human donor to a human recipient, alternative sources of pancreatic tissue for transplantation have been investigated. Several groups of investigators have conducted research involving the use of pancreatic cells and tissue from animal sources, such as swine, for transplantation. See e.g., Korsgren, O. et al. (1993) Surgery 113:205–214; Braesch, M. K. et al. (1992) Transplant. Proc. 24(2):679–680; Groth, C. G. et al. (1992) Transplant. Proc. 24(3):972–973; Liu, X. et al. (1991) Diabetes 40:858–866; Korsgren, O. et al. (1991) Diabetologia 34:379–386; Yoneda, K. et al. (1989) Diabetes 38 (Supp. 1):213–216; Wilson, J. D. et al. (1989) Diabetes 38 (Suppl. 1):217–219; Korsgren, O. et al. (1989) Diabetes 38 (Suppl. 1):209–212; Korsgren, O. et al. (1988) Transplantation 45(3):509–514; Sasaki, N. et al. (1984) Transplantation 38(4):335–340. Several of these investigators report transplantation of pancreatic tissue samples containing insulin-secreting and at least partially differentiated porcine pancreatic cells into xenogeneic subjects after short-term culture. However, these short-term cultures of pancreatic cells often display eventual necrosis (Thompson, S. C. et al. (1990) Transplantation 49(3):571–581), developmental stagnation (Liu, X. et al. (1991) Diabetes 40:858–866; Korsgren, O. et al. (1989) Diabetes 38 (Suppl. 1):209–212; Korsgren, O. et al. (1988) Transplantation 45(3):509–514), decreased proliferation (Liu, X. et al. (1991) Diabetes 40:858–866; Korsgren, O. et al. (1988) Transplantation 45(3):509–514), and decreased insulin production (Yoneda, K. et al. (1989) Diabetes 38 (Supp. 1):213–216; Korsgren, O. et al. (1988) Transplantation 45(3):509–514).

SUMMARY OF THE INVENTION

The present invention provides porcine pancreatic cell(s) which can be used to generate populations of cells useful for transplantation into diabetic subjects. The porcine pancreatic cells of the invention are capable of proliferating in vitro and in vivo and are insulin-secreting after transplantation into a recipient subject. Accordingly, the invention pertains to isolated non-insulin-secreting porcine pancreatic cells having the ability to differentiate into insulin-secreting cells upon introduction into a xenogeneic subject. In one embodiment, the non-insulin-secreting porcine pancreatic cells are embryonic pancreatic cells isolated during certain stages of gestational development. It has been discovered that such porcine embryonic pancreatic cells can be maintained in culture if sub-confluent and will proliferate for long periods of time, e.g., six months or more, without forming pseudo islet-like aggregates. Preferably, the pancreatic cells are obtained from embryonic pigs at an early stage of development (i.e., prior to formation of islets in vivo) and are maintained in culture to allow cell proliferation without substantial differentiation into islet-like aggregates. Moreover, the culture is not diluted out by non-insulin-producing cells, e.g., endothelial cells, which are involved in islet formation. Furthermore, proliferation of the cultured pancreatic cells can be substantially augmented by adding certain embryonic proliferating agents to the culture. These embryonic proliferating agents can decrease the doubling time of the cells by almost two-fold. When the cells are allowed to reach confluence, they begin to form pseudo islet-like aggregates which produce insulin, glucagon, and somatostatin.

Thus, large populations of non-insulin-secreting porcine pancreatic cells capable of proliferating and differentiating to produce insulin-secreting cells upon introduction into a subject can be prepared in an economical and time-efficient manner. The porcine pancreatic cells of the invention can, therefore, serve as a convenient and plentiful source of cells for administration to subjects having diseases caused by insufficient activity of a pancreatic hormone, e.g, insulin, e.g., Type I or Type II diabetes, or enzyme.

Accordingly, the instant invention pertains to an isolated porcine pancreatic cell and a population of porcine pancreatic cells suitable for administration to a xenogeneic subject, particularly a human subject. The isolated porcine pancreatic cell, alone or in a population, produces glucagon and somatostatin in certain embodiments, but does not secrete insulin. Upon introduction into a xenogeneic subject, however, the porcine pancreatic cell proliferates and differentiates to form a population of insulin-secreting cells. Preferred porcine pancreatic cells are embryonic porcine pancreatic cells obtained from an embryonic pig at a selected gestational age. The preferred gestational age of embryonic swine from which to obtain pancreatic cells suitable for transplantation into xenogeneic subjects, particularly humans, was determined to be between about twenty (28) and about forty (40) days, more preferably between about thirty (30) and thirty-five (35) days, most preferably between about thirty-one (31) and about thirty-five (35) days of gestation. It is preferred that the porcine pancreatic cells be obtained from a pig which is essentially free from organisms or substances which are capable of transmitting infection or disease to a xenogeneic recipient of the cells as described herein. Typically, the porcine pancreatic cells are isolated from a pig which is essentially free from at least one organism selected from the group consisting of parasites, bacteria, mycoplasma, and viruses. In addition, the porcine pancreatic cells can be modified as described herein. The porcine pancreatic cells of the invention can be grown as a cell culture in a medium suitable to support the growth of the cells. In addition, the porcine pancreatic cells can be inserted into a delivery device, e.g., a syringe, which facilitates the introduction of the cells into a subject.

The invention further pertains to a porcine pancreatic cell and an isolated population of such cells which, in unmodified form, have at least one antigen on the cell surface which is capable of stimulating an immune response against the cell(s) in a xenogeneic subject, for example, a human. The antigen on the surface of the porcine pancreatic cell(s) is altered to inhibit rejection of the cell(s) when introduced into a xenogeneic subject. In one embodiment, the cell surface antigen which is altered is an MHC class I antigen. This MHC class I antigen can be contacted, prior to transplantation into a xenogeneic subject with at least one MHC class I antibody, or a fragment or derivative thereof, which binds to the MHC class I antigen on the cell surface but does not activate complement or induce lysis of the cell. One example of an MHC class I antibody is an MHC class I F(ab')$_2$ fragment, such as an MHC class I F(ab')$_2$ fragment of a monoclonal antibody PT85. In one embodiment, the porcine pancreatic cells are obtained from embryonic pigs of the preferred gestational ages described herein. Porcine pancreatic cells to be modified in this manner can be obtained from a pig which is essentially free from organisms or substances which are capable of transmitting infection or disease to a xenogeneic recipient of the cells as described herein.

A further aspect of the invention pertains to methods of promoting or inducing proliferation of embryonic porcine pancreatic cells in which the cells are contacted with at least one embryonic proliferating agent which promotes or induces proliferation of the cells in vitro and/or in vivo. Preferred embryonic proliferating agents for promoting or inducing proliferation of embryonic porcine pancreatic cells include platelet-derived growth factor (PDGF) and epidermal growth factor (EGF). Other embryonic proliferating agents include growth factors for which the embryonic porcine pancreatic cells of a certain gestational age (e.g., between about 31 and 35 days of gestation) express a receptor.

The invention also provides methods of isolating and promoting proliferation of porcine pancreatic cells in vitro prior to the administration of the cells to a xenogeneic subject. These methods typically include isolating porcine pancreatic cells from an embryonic pig and contacting the cells with an embryonic proliferating agent, such as PDGF, EGF or growth factors for which the embryonic porcine pancreatic cells express a receptor, which promotes proliferation of the cells. The cells are preferably isolated from an embryonic pig from about day 31 to about day 35 of gestation. In one embodiment the porcine pancreatic cells are non-insulin-secreting cells which have the ability to differentiate into insulin-secreting cells upon introduction into a xenogeneic subject. The cells can be administered to the xenogeneic subject prior to or after in vitro formation of insulin-secreting islet-like aggregates.

The invention still further provides methods of treating diseases characterized by insufficient insulin activity, e.g, Type I and Type II diabetes, in a subject, e.g., a human, having such a disease. In one embodiment, a subject having the disease is administered an amount of a population of non-insulin-secreting porcine pancreatic cells which are obtained from an embryonic pig, e.g., cells from an embryonic pig between about day 31 and day 35 of gestation, having the ability to differentiate into insulin-secreting cells following administration to the subject. These cells can be modified as described herein prior to introduction into the subject. In another embodiment, a subject having a disease characterized by insufficient insulin activity is administered a population of modified porcine pancreatic cells of the invention or a population of porcine pancreatic cells obtained from pigs which are essentially free from organisms and substances which are capable of transmitting infection or disease to the subject. These methods can further include the step of administering an immunosuppressive agent to the subject.

BRIEF DESCRIPTION OF THE DRAWINGS

FIG. 1A is a phase micrograph of fetal pig pancreatic cells in monolayer prior to formation of islet-like clusters. No insulin staining can be detected in these cells at this time. FIG. 1B is a phase micrograph of fetal pig pancreatic cells that were allowed to form islet-like clusters (indicated by arrows) and stained positive for insulin.

FIG. 2A is a section from transplanted kidney showing the graft stained with aldehyde-fuchsin. Insulin-containing cells stain darkly and can be seen scattered throughout the graft. FIG. 2B is a section from the same graft stained with antibodies which recognize insulin. Again, the insulin-containing cells within the graft stain more darkly than the other cells. In both figures, the insulin-positive cells are indicated by arrows, the donor graft is marked (G), and the recipient mouse kidney is marked (K).

DETAILED DESCRIPTION OF THE INVENTION

I. ISOLATED CELLS AND CELL POPULATIONS OF THE INVENTION

Figure 1A:
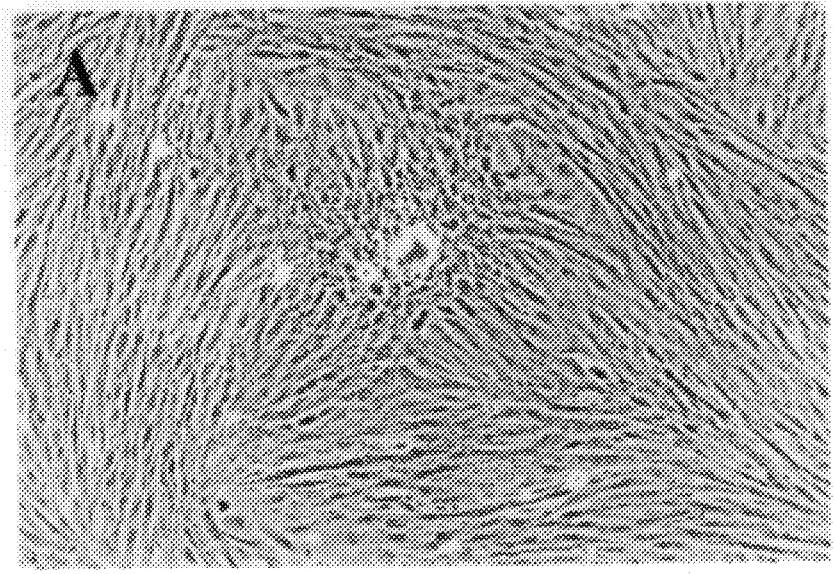
FIGS. 1A–1B depict insulin staining of fetal pig pancreatic cells in culture.

A. Non-Insulin-Secreting Porcine Pancreatic Cells Suitable for Administration to Xenogeneic Subjects This invention features an isolated non-insulin-secreting porcine pancreatic cell having the ability to differentiate into an insulin-secreting cell upon introduction into a xenogeneic subject. These cells can be used to treat diseases, such as Type I and Type II diabetes, which are characterized by insufficient activity of the hormones, e.g., insulin, and enzymes produced by the pancreas. As used herein, the term "isolated" refers to a cell which has been separated from its natural environment. This term includes gross physical separation from its natural environment, e.g., removal from the donor animal, e.g., a pig, and alteration of the cell's relationship with the neighboring cells with which it is in direct contact by, for example, dissociation. Isolation does not refer to a cell which is in a tissue section, is cultured as part of a tissue section, or is transplanted in the form of a tissue section. When used to refer to a population of porcine pancreatic cells, the term "isolated" includes populations of cells which result from proliferation of the isolated cells of the invention.

When isolated from a donor swine, the pancreatic cells of the invention are non-insulin-secreting. The phrase "non-insulin-secreting" refers to cells which do not deposit detectable or therapeutically significant amounts of insulin into their surroundings, e.g., tissue fluid or culture medium. Therapeutically significant amounts of insulin include amounts which are capable of reducing or alleviating at least one adverse effect or symptom of a disease characterized by insufficient insulin activity when an appropriate number of the insulin-secreting cells are introduced in a subject having such a disease. However, the isolated cells have the ability to differentiate into insulin-secreting cells in vitro or upon introduction into a subject. In one embodiment, the non-insulin-secreting porcine pancreatic cells are further characterized by the ability to produce detectable amounts of glucagon and/or somatostatin upon isolation from the donor swine. The pancreatic cells of the invention, when administered to a xenogeneic subject, "proliferate", a term which is used herein to mean reproduce or multiply, to produce or form a population i.e., a group of two or more cells. Differentiation, as used herein, refers to cells which have acquired functions different from and/or in addition to those that the cells originally possessed. For example, an non-insulin porcine pancreatic cell can differentiate, under specific conditions, into a cell which secretes insulin. As used herein, the phrase "secrete insulin" refers to cells which deposit insulin into their surroundings, e.g., tissue fluid, e.g, blood, or culture medium. A common method for analyzing tissue fluid or culture media for insulin-secretion is by radioimmunoassay. See Heding, L. G. (1972) *Diabetologia* 8:260.

The term "subject" is intended to include mammals, particularly humans, susceptible to diseases characterized by insufficient insulin activity. The term "subject" also includes mammals in which an immune response is elicited against allogeneic or xenogeneic cells. Examples of subjects include primates (e.g., humans, and monkeys). A "xenogeneic subject" (also referred to herein as "recipient subject" or "recipient") as used herein is a subject into which cells of another species are introduced or are to be introduced.

The pancreas is a mixed exocrine and endocrine gland. The exocrine portion is composed of several serous cells surrounding a lumen. These cells synthesize and secrete digestive enzymes such as trypsinogen, chymotrypsinogen, carboxypeptidase, ribonuclease, deoxyribonuclease, triacylglycerol lipase, phospholipase $A_2$, elastase, and amylase. The endocrine portion of the pancreas is composed of the islets of Langerhans. The islets of Langerhans appear as rounded clusters of cells embedded within the exocrine pancreas. Four different types of cells-$\alpha$, $\beta$, $\delta$, and $\phi$-have been identified in the islets. The $\alpha$ cells constitute about 20% of the cells found in pancreatic islets and produce the hormone glucagon. Glucagon acts on several tissues to make energy available in the intervals between feeding. In the liver, glucagon causes breakdown of glycogen and promotes gluconeogenesis from amino acid precursors. The $\delta$ cells produce somatostatin which acts in the pancreas to inhibit glucagon release and to decrease pancreatic exocrine secretion. The hormone pancreatic polypeptide is produced in the $\phi$ cells. This hormone inhibits pancreatic exocrine secretion of bicarbonate and enzymes, causes relaxation of the gallbladder, and decreases bile secretion. The most abundant cell in the islets, constituting 60–80% of the cells, is the $\beta$ cell, which produces insulin. Insulin is known to cause the storage of excess nutrients arising during and shortly after feeding. The major target organs for insulin are the liver, muscle, and fat-organs specialized for storage of energy.

The language "pancreatic cell" refers to a cell which can produce a hormone or enzyme normally produced by a pancreatic cell, e.g., an at least partially differentiated $\alpha$, $\beta$, $\delta$, or $\phi$ cell, and a cell, e.g., a pancreatic precursor cell, which can develop into a cell which can produce a hormone or enzyme normally produced by a pancreatic cell. In one embodiment, the porcine pancreatic cells are characterized by the ability to produce glucagon and/or somatostatin upon isolation from a donor swine. The pancreatic cells of the invention can also be cultured prior to administration to a subject under conditions which promote cell proliferation and differentiation. These conditions include culturing the cells to allow proliferation and confluence in vitro at which time the cells form pseudo islet-like aggregates or clusters and secrete insulin, glucagon, and somatostatin.

Pancreatic cells of the invention are obtained from the pancreas of a donor swine (also referred to herein as "pig") such as, for example, a swine which is essentially pathogen-free as described herein. In a preferred embodiment, the pancreatic cells are obtained from the primordial pancreas (also referred to herein as "fetal pancreas" and "embryonic pancreas") of an embryonic donor swine and preferably at a selected gestational age. The selected gestational ages (the total gestation time for pig is approximately 115 days) for obtaining primordial pancreatic cells are determined based on the following criteria: the ability of the embryonic porcine pancreas structure to be identified; the viability of the cells upon isolation from the donor pig, the ability of the cells to proliferate in culture; the ability of the cells to remain undifferentiated (i.e., non-insulin secreting) in culture; and the ability of the cells to differentiate (i.e., secrete pancreatic hormones, e.g., insulin, and enzymes) upon introduction into a recipient subject. The preferred gestational age of embryonic swine from which to obtain pancreatic cells suitable for introduction into xenogeneic subjects, particularly humans, was determined to be between about twenty (28) and about forty (40) days, more preferably about thirty (30) and about thirty-five (35) days, most preferably about thirty-one (31) and about thirty-five (35) days of gestation. Earlier than about days 28–30 of gestation, the primordial pancreas in embryonic swine is not as easy to identify. Later than about days 35–36 of gestation, the pancreatic cells are not as easy to dissociate and are marginally proliferative to nonproliferative in culture. Thus, the preferred range for isolation of porcine pancreatic cells was determined to be between about thirty-one (31) and about thirty-five (35) days of development. This corresponds to fetal crown-to-rump (CRL) length of between 25 and 45 mm.

Pancreatic cells within the preferred embryonic age range have some or all of the following characteristics: the cells form a monolayer of adherent cells (i.e., they adhere to culture substrate, e.g., culture dish, forming fibroblast-like cells) when subconfluent; the cells (as a subconfluent monolayer of cells) are uniform in morphology, e.g., there are few if any contaminating cells (e.g., cells that are associated with duct formation or cells that do not secrete or do not develop into cells that secrete pancreatic hormones or enzymes) and stain positive for glucagon and somatostatin but not for insulin; the cells are capable of proliferating for an extended period of time under appropriate conditions, e.g., several months (six or more), in a growth medium and the cells are maintained subconfluent; when the cells are allowed to reach confluence, they begin to form pseudo islet-like cell aggregates spontaneously and stain positive for insulin, glucagon, and somatostatin. Prior to the formation of islet-like aggregates, there is no detectable insulin staining. See FIG. 1A. The formation of islet-like aggregates is necessary for the expression of insulin. See FIG. 1B.

Accordingly, this invention also features a population or a group of two or more cells, of non-insulin-secreting porcine pancreatic cells having the ability to differentiate into insulin-secreting cells upon introduction into a xenogeneic subject. The cells of the population are typically obtained from a selected area of the developing gut, e.g., the primordial pancreas, which is typically identified as an unlobulated solid tissue located around the duodenal loop just below the stomach.

The cells of the invention can be grown as a cell culture, i.e., as a population of cells which grow in vitro, in a medium suitable to support the growth of the cells. The characteristics of the cells when grown as cell cultures are described herein in detail. Media which can be used to support the growth of porcine pancreatic cells include mammalian cell culture media, such as those produced by Gibco BRL (Gaithersburg, Md.). See 1994 Gibco BRL Catalogue & Reference Guide. The medium can be serum-free but is preferably supplemented with animal serum such as fetal calf serum. A preferred medium is RPMI-1640 supplemented with fetal calf serum. The medium can be further supplemented with the embryonic proliferating agents described herein to induce or promote proliferation of the porcine pancreatic cells.

As common methods of administering pancreatic cells to subjects, particularly human subjects, which are described in detail herein, include injection or implantation of the cells into target sites in the subjects, the cells of the invention can be inserted into a delivery device which facilitates introduction by, injection or implantation, of the cells into the subjects. Such delivery devices include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The porcine pancreatic cells of the invention can be inserted into such a delivery device, e.g., a syringe, in different forms. For example, the cells can be suspended in a solution or embedded in a support matrix when contained in such a delivery device. As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating porcine pancreatic cells as described herein in a pharmaceutically acceptable carrier or diluent and, as required, other ingredients enumerated above, followed by filtered sterilization.

Support matrices in which the porcine pancreatic cells can be incorporated or embedded include matrices which are recipient-compatible and which degrade into products which are not harmful to the recipient. Natural and/or synthetic biodegradable matrices are examples of such matrices. Natural biodegradable matrices include plasma clots, e.g., derived from a mammal, and collagen matrices. Synthetic biodegradable matrices include synthetic polymers such as polyanhydrides, polyorthoesters, and polylactic acid. Other examples of synthetic polymers and methods of incorporating or embedding cells into these matrices are known in the art. See e.g., U.S. Pat. No. 4,298,002 and U.S. Pat. No. 5,308,701. These matrices provide support and protection for the fragile pancreatic cells in vivo and are, therefore, the preferred form in which the pancreatic cells are introduced into the recipient subjects.

B. Modified Porcine Pancreatic Cells and Isolated Populations of Modified Porcine Pancreatic Cells A further aspect of the invention is a porcine pancreatic cell which, in unmodified form, has at least one antigen on the cell surface which is capable of stimulating an immune response against the cell in a xenogeneic subject. To inhibit rejection of the cell when introduced into the xenogeneic subject, the antigen on the cell surface is altered prior to transplantation. In an unaltered state, the antigen on the cell surface stimulates an immune response against the cell when the cell is administered to a subject. By altering the antigen, the normal immunological recognition of the porcine pancreatic cell by the immune system cells of the recipient is disrupted and additionally, "abnormal" immunological recognition of this altered form of the antigen can lead to porcine pancreatic cell-specific long term unresponsiveness in the recipient. It is likely that alteration of an antigen on the porcine pancreatic cell prior to introducing the cell into a subject interferes with the initial phase of recognition of the porcine pancreatic cell by the cells of the host's immune system subsequent to administration of the cell. Furthermore, alteration of the antigen can induce immunological nonresponsiveness or tolerance, thereby preventing the induction of the effector phases of an immune response (e.g., cytotoxic T cell generation, antibody production etc.) which are ultimately responsible for rejection of foreign cells in a normal immune response. As used herein, the term "altered" encompasses changes that are made to at least one porcine pancreatic cell antigen(s) which reduce the immunogenicity of the antigen to thereby interfere with immunological recognition of the antigen(s) by the recipient's immune system. An example of an alteration of a porcine pancreatic cell antigen is binding of a second molecule to the antigen. The second molecule can decrease or prevent recognition of the antigen as a foreign antigen by the recipient subject's immune system.

Antigens to be altered according to the current invention include antigens on a porcine pancreatic cell which can interact with an immune cell in a xenogeneic (or allogeneic) recipient subject and thereby stimulate a specific immune response against the porcine pancreatic cell in the recipient. The interaction between the antigen and the immune cell can be an indirect interaction (e.g., mediated by soluble factors which induce a response in the immune cell, e.g., humoral mediated) or, preferably, is a direct interaction between the antigen and a molecule present on the surface of the immune cell (i.e., cell-cell mediated). As used herein, the term "immune cell" is intended to include T lymphocytes, B lymphocytes, monocytes and other antigen presenting cells. In a preferred embodiment, the antigen is one which interacts with a T lymphocyte in the recipient (e.g., the antigen normally binds to a receptor on the surface of a T lymphocyte).

In one embodiment, the antigen on the porcine pancreatic cell to be altered is an MHC class I antigen. Alternatively, an adhesion molecule on the cell surface, such as ICAM-1, can be altered. An antigen which stimulates a cellular immune response against the cell, such as an MHC class I antigen, can be altered prior to transplantation by contacting the cell with a molecule which binds to the antigen. A preferred molecule for binding to the antigen is an antibody, or fragment thereof (e.g., an MHC class I antibody, or fragment thereof). A preferred antibody fragment is an $F(ab')_2$ fragment. Polyclonal or, more preferably, monoclonal antibodies can be used. Other molecules which can be used to alter an antigen (e.g., an MHC class I antigen) include peptides and small organic molecules which bind to the antigen. Furthermore, two or more different epitopes on the same or different antigens on the cell surface can be altered. A particularly preferred monoclonal antibody for alteration of MHC class I antigens on porcine pancreatic cells is PT85 (commercially available from Veterinary Medicine Research Development, Pullman, Wash.). PT85 can be used alone to alter MHC class I antigens or, if each antibody is specific for a different epitope, PT85 can be used in combination with another antibody known to bind MHC class I antigens to alter the antigens on the cell surface. Suitable methods for altering a surface antigen on a cell for transplantation are described in greater detail in Faustman and Coe (1991) *Science* 252:1700–1702 and PCT publication WO 92/04033. Methods for altering multiple epitopes on a surface antigen on a cell for transplantation are described in greater detail in U.S. patent application Ser. No. 08/220,741, filed Mar. 31, 1994, the contents of which are incorporated herein by reference. The altered (also referred to herein as "modified") porcine cells can comprise an isolated population of cells. The characteristics of such populations are described above. The pancreatic cells to be modified can be obtained from donor swine at the gestational ages described herein. Preferably, the modifications described herein are performed on porcine pancreatic cells prior to formation of islet-like aggregates or clusters. Preferred donor swine are those which are essentially pathogen-free as described herein.

C. Porcine Pancreatic Cells and Isolated Populations of Porcine Pancreatic Cells Obtained from Essentially Pathogen-Free Swine The invention also features a porcine pancreatic cell obtained from a swine which is essentially free from organisms or substances which are capable of transmitting infection or disease to a xenogeneic recipient, e.g., a human recipient, of the cells. Typically, porcine pancreatic cells are obtained from a swine which is essentially free from pathogens which affect humans. For example, the pathogens from which the swine are free include, but are not limited to, one or more of pathogens from the following categories of pathogens: parasites, bacteria, mycoplasma, and viruses. The swine can be free from, for example, parasites such as toxoplasma and eperytherozoon, or mycoplasma, such as *M. hyopneumonia*. Examples of bacteria from which the swine can be free include brucella, listeria, mycobacterium TB, leptospirillum, and haemophilus suis. Additionally, the swine can be free from viruses such as zoonotic viruses (viruses which can be transferred from pigs to man under natural conditions), viruses that can cross the placenta in pregnant sows, and neurotrophic viruses. Zoonotic viruses include, for example, a virus in the rabies virus group, a herpes-like virus which causes pseudorabies, encephalomyocarditis virus, swine influenza Type A, transmissible gastroenteritus virus, parainfluenza virus 3 and vesicular stomatitis virus. Viruses that can cross the placenta include, for example, viruses that cause porcine respiratory reproductive syndrome, a virus in the rabies virus group, a herpes-like virus which causes pseudorabies, parvovirus, a virus that causes swine vesicular disease, techen (porcine polio virus), hemmaglutinating encephalomyocarditus, cytomegalovirus, suipoxvirus, and swine influenza type A. Neurotrophic viruses include, for example, a virus in the rabies virus group, a herpes-like virus which causes pseudorabies, parvovirus, encephalomyocarditus virus, a virus which causes swine vesicular disease, porcine poliovirus (techen), a virus which causes hemmaglutinating encephalomyocarditus, adenovirus, parainfluenza 3 virus. Specific examples of viruses from which the swine are free include: a virus which causes (or results in) porcine respiratory reproductive syndrome, a virus in the rabies virus group, a herpes-like virus which causes pseudorabies, parvovirus, encephalomyocarditus virus, a virus which causes swine vesicular disease, porcine poliovirus (techen), a virus which causes hemmaglutinating encephalomyocarditus, cytomegalovirus, suipoxvirus, swine influenza type A, adenovirus, transmissible gastroenteritus virus, a virus which causes bovine viral diarrhea, parainfluenza virus 3, and vesicular stomatitis virus.

In one embodiment, the pigs from which pancreatic cells are isolated are essentially free from the following organisms: Toxoplasma, eperythrozoon, brucella, listeria, mycobacterium TB, leptospirillum, haemophilus suis, *M. Hyopneumonia*, a virus which causes porcine respiratory reproductive syndrome, a virus which causes rabies, a virus which causes pseudorabies, parvovirus, encephalomyocarditis virus, a virus which causes swine vesicular disease, porcine polio virus (techen), a virus which causes hemagglutinating encephalomyocarditus, suipoxvirus, swine influenza type A, adenovirus, transmissible gastroenteritis virus, a virus which causes bovine viral diarrhea, and vesicular stomatitis virus. The phrase "essentially free from organisms or substances which are capable of transmitting infection or disease to a xenogeneic recipient" (also referred to herein as "essentially pathogen-free") when referring to a swine from which cells are isolated means that swine does not contain organisms or substances in an amount which transmits infection or disease to a xenogeneic recipient, e.g. a human. Example III provides representative, but not limiting examples of methods for selecting swine which are essentially free from various pathogens. The pancreatic cells of the invention can be isolated from embryonic or post-natal swine which are determined to be essentially free of such organisms. These swine are maintained under suitable conditions until used as a source of pancreatic cells.

Preferred gestational ages of the swine from which these cells are obtained are described in detail herein. Porcine pancreatic cells obtained from essentially pathogen-free swine can additionally be modified to reduce the immunogenicity of the cells following administration to a xenogeneic subject as described herein.

II. METHODS OF THE INVENTION

A. Methods of Isolating Porcine Pancreatic Cells from Embryonic Swine

Other aspects of the invention include methods of isolating porcine pancreatic cells suitable for administration to a xenogeneic subject. These methods typically include isolating porcine pancreatic cells from a swine, e.g., an embryonic swine between about day thirty-one (31) and day thirty-five (35) of gestation, and optionally contacting the porcine pancreatic cells with at least one embryonic proliferating agent which promotes or induces cell proliferation in vitro or in vivo prior to introduction of the cells into a subject. Porcine pancreatic cells isolated according to the methods of the invention can be further modified as described herein for introduction into a xenogeneic subject.

Methods of isolating pancreatic cells from primordial gut tissue are known in the art. For example, solid pancreatic tissue samples can be dissected from surrounding gut tissue, e.g., by dissecting the tissue under a dissecting microscope. The cells in the pancreatic tissue sample can then dissociated by mechanical means, e.g., chopping and/or successive pipette trituration, or by chemical means, e.g., by use of enzymes, such as trypsin or collagenase. The swine which are employed in the method of the invention as a source of pancreatic cells include embryonic swine (swine fetuses), postnatal swine, pathogen-free embryonic swine, and pathogen-free postnatal swine. If an embryonic pathogen-free swine is to be used as a source of pancreatic cells, semen from a boar which has been tested to be essentially free of disease-transmitting organisms is employed to artificially inseminate a female swine which is essentially free from such organisms. At about thirty-one (31) to about thirty-five (35) days of gestation, a hysterectomy is performed under appropriate conditions of sterility and the fetuses are thereafter removed in their individual amniotic sacs. Appropriate pancreatic cells or tissue are thereafter recovered, as described, for example, in Example I herein, under appropriate conditions of sterility.

The methods of isolating porcine pancreatic cells suitable for administration to a xenogeneic subject can, optionally, further include one or more of the following steps: administering the porcine pancreatic cells to a xenogeneic subject prior to formation of insulin-secreting islet-like aggregates or clusters in culture; administering the porcine pancreatic cells to a xenogeneic subject after the cells form insulin-secreting islet-like aggregates or clusters in culture; and administering the porcine pancreatic cells to a xenogeneic subject as non-insulin-secreting cells which are capable of differentiating in vivo to form insulin-secreting cells. The in vitro and in vivo characteristics of the porcine pancreatic cells of the invention are described in further detail herein.

B. Methods of Promoting or Inducing Proliferation of Porcine Pancreatic Cells

Further aspects of the invention include methods of promoting or inducing proliferation of embryonic porcine pancreatic cells. These methods include contacting embryonic porcine pancreatic cells, in vitro or in vivo, with at least one embryonic proliferating agent, which promote(s) or induce(s) proliferation of the cells. The phrase "embryonic proliferating agent" is intended to include agents which promote or enhance the proliferation of embryonic porcine pancreatic cells. Thus, embryonic proliferating agents which promote or induce proliferation of the porcine pancreatic cells include substances which increase the number of times that an embryonic porcine pancreatic cell multiplies or reproduces to form two cells (e.g., doubling time) in a given period of time. Specific examples of growth factors include PDGF and EGF and their equivalents. When the porcine pancreatic cells of the invention are contacted with both PDGF and EGF, their doubling time can be decreased by about 30–50% (e.g., 80 hours without growth factors vs. 58 hours with growth factors). It should be understood that the phrase "embryonic proliferating agent" also includes growth factors for which embryonic porcine pancreatic cells of a certain gestational age (e.g., between about 31 to about 35 days) express a receptor. The methods of the invention allow the efficient production of large numbers of porcine pancreatic cells for introduction into xenogeneic subjects. This is an important as about ten to fifty to about one hundred fifty million porcine pancreatic cells are required to treat one human having a disease characterized by insufficient insulin activity. According to the methods of this invention, one fetal pig yields about one and a half million pancreatic cells. Thus, about ten doublings (about 24 days) of these fetal pancreatic cells results in a number of cells sufficient for introduction into a human subject. If several fetal pigs, e.g., a litter of fetal pigs, are used as donors of pancreatic cells, sufficient numbers of cells can be generated for introduction into a human recipient in a matter of days.

C. Methods of Treating Diseases Characterized by Insufficient Insulin Activity Using Porcine Pancreatic Cells Still further aspects of the invention include methods of treating diseases characterized by insufficient insulin activity in a subject, particularly a human subject. These methods include administering to a xenogeneic subject, an isolated population of non-insulin-secreting porcine pancreatic cells having the ability to differentiate to form insulin-secreting cells after administration to the subject. Such populations of cells are described in detail herein. The terms "introduction", "administration", and "transplantation" are used interchangeably herein and refer to delivery of cells to a xenogeneic subject by a method or route which delivers the cells to a desired location. The term "treating" as used herein includes reducing or alleviating at least one adverse effect or symptom, e.g, absolute or relative insulin deficiency, fasting hyperglycemia, glycosuria, development of atherosclerosis, microangiopathy, nephropathy, and neuropathy, of diseases characterized by insufficient insulin activity. As used herein, the language "diseases characterized by insufficient insulin activity" include diseases in which there is an abnormal utilization of glucose due to abnormal insulin function. Abnormal insulin function includes any abnormality or impairment in insulin production, e.g., expression and/or transport through cellular organelles, such as insulin deficiency resulting from, for example, loss of $\beta$ cells as in IDDM (Type I diabetes), secretion, such as impairment of insulin secretory responses as in NIDDM (Type II diabetes), form of the insulin molecule itself, e.g., primary, secondary or tertiary structure, effects of insulin on target cells, e.g., insulin-resistance in bodily tissues, e.g., peripheral tissues, and responses of target cells to insulin. See Braunwald, E. et al. eds. Harrison's Principles of Internal Medicine, Eleventh Edition (McGraw-Hill Book Company, New York, 1987) pp. 1778–1797; Robbins, S. L. et al. Pathologic Basis of Disease, 3rd Edition (W. B. Saunders Company, Philadelphia, 1984) p. 972 for further descriptions of abnormal insulin activity in IDDM and NIDDM and other forms of diabetes.

The porcine pancreatic cells are administered to the subject by any appropriate route which results in delivery of the cells to a desired location in the subject where the cells can proliferate and secrete a pancreatic hormone, e.g., insulin, or enzyme. Preferred locations for pancreatic cell administration include those which rapidly vascularize. Common methods of administering pancreatic cells to subjects, particularly human subjects, include implantation of cells in a pouch of omentum (Yoneda, K. et al. (1989) *Diabetes* 38 (Suppl. 1):213–216), intraperitoneal injection of the cells, (Wahoff, D. C. et al. (1994) *Transplant. Proc.* 26:804), implantation of the cells under the kidney capsule of the subject (See, e.g., Liu, X. et al. (1991) *Diabetes* 40:858–866; Korsgren, O. et al. (1988) *Transplantation* 45(3):509–514; Simeonovic, D. J. et al. (1982) *Aust. J. Exp. Biol. Med. Sci.* 60:383), and intravenous injection of the cells into, for example, the portal vein (Braesch, M. K. et al. (1992) *Transplant. Proc.* 24(2):679–680; Groth, C. G. et al. (1992) *Transplant. Proc.* 24(3):972–973). To facilitate transplantation of the pancreatic cells under the kidney capsule, the cells can be embedded in a plasma clot prepared from, e.g., plasma from the recipient subject (Simeonovic, D. J. et al. (1982) *Aust. J. Exp. Biol. Med. Sci.* 60:383) or a collagen matrix. Cells can be administered in a pharmaceutically acceptable carrier or diluent as described herein.

This invention further pertains to methods of treating diseases characterized by insufficient insulin activity in a subject, particularly a human subject, in which an isolated population of porcine pancreatic cells obtained from an embryonic pig between about day 31 and day 35 of gestation, which form insulin-secreting islet-like aggregates or clusters in culture, and which secrete insulin after administration to the subject is administered to the subject. As described herein, pancreatic cells obtained from embryonic pigs between about day 31 and 35 can be cultured as a monolayer of adherent non-insulin secreting cells. When these cells are allowed to reach confluence, they form islet-like aggregates or clusters and begin to secrete pancreatic hormones, such as insulin, glucagon, and somatostatin, and enzymes. At this point, such aggregates can be isolated, pooled, and administered to a recipient subject wherein they secrete insulin. About 100,000 to 500,000 aggregates, each of which contains about 300 to 500 cells, can be used to treat one human. This number of cells can be generated from one pig fetus after about ten doublings (about 24 days) or from a litter (6–10) of fetal pigs after only a few days of doubling (about 2–10 days). Additional porcine pancreatic cells and isolated populations of such cells which can be administered to a xenogeneic subject according to this method include embryonic porcine pancreatic cells, embryonic porcine pancreatic cells obtained from an essentially pathogen-free pig, modified porcine pancreatic cells, modified porcine pancreatic cells obtained from an essentially pathogen-free pig, modified embryonic porcine pancreatic cells, and modified embryonic porcine pancreatic cells obtained from an essentially pathogen-free pig. These and other porcine pancreatic cells are described in detail herein.

The porcine pancreatic cells of the invention can be administered to a xenogeneic subject having a disease characterized by insufficient insulin activity in combination with administration of an agent which inhibits T cell activity in the subject. As used herein, an agent which inhibits T cell activity is defined as an agent which results in removal (e.g., sequestration) or destruction of T cells within a subject or inhibits T cell functions within the subject (i.e., T cells may still be present in the subject but are in a non-functional state, such that they are unable to proliferate or elicit or perform effector functions, e.g. cytokine production, cytotoxicity etc.). The term "T cell" encompasses mature peripheral blood T lymphocytes. The agent which inhibits T cell activity may also inhibit the activity or maturation of immature T cells (e.g., thymocytes).

A preferred agent for use in inhibiting T cell activity in a recipient subject is an immunosuppressive drug. The term "immunosuppressive drug or agent" is intended to include pharmaceutical agents which inhibit or interfere with normal immune function. A preferred immunsuppressive drug is cyclosporin A. Other immunosuppressive drugs which can be used include FK506, and RS-61443. In one embodiment, the immunosuppressive drug is administered in conjunction with at least one other therapeutic agent. Additional therapeutic agents which can be administered include steroids (e.g., glucocorticoids such as prednisone, methyl prednisolone and dexamethasone) and chemotherapeutic agents (e.g., azathioprine and cyclosphophamide). In another embodiment, an immunosuppressive drug is administered in conjunction with both a steroid and a chemotherapeutic agent. Suitable immunosuppressive drugs are commercially available (e.g., cyclosporin A is available from Sandoz, Corp., East Hanover, N.J.).

An immunsuppressive drug is administered in a formulation which is compatible with the route of administration. Suitable routes of administration include intravenous injection (either as a single infusion, multiple infusions or as an intravenous drip over time), intraperitoneal injection, intramuscular injection and oral administration. For intravenous injection, the drug can be dissolved in a physiologically acceptable carrier or diluent (e.g., a buffered saline solution) which is sterile and allows for syringability. Dispersions of drugs can also be prepared in glycerol, liquid polyethylene glycols, and mixtures thereof and in oils. Convenient routes of administration and carriers for immunsuppressive drugs are known in the art. For example, cyclosporin A can be administered intravenously in a saline solution, or orally, intraperitoneally or intramuscularly in olive oil or other suitable carrier or diluent.

An immunosuppressive drug is administered to a recipient subject at a dosage sufficient to achieve the desired therapeutic effect (e.g., inhibition of rejection of transplanted cells). Dosage ranges for immunosuppressive drugs, and other agents which can be coadministered therewith (e.g., steroids and chemotherapeutic agents), are known in the art (See e.g., Freed et al. *New Engl. J. Med.* (1992) 327:1549: Spencer et al. (1992) *New Engl. J. Med.* 327:1541; Widner et al. (1992) *New Engl. J. Med.* 327:1556; Lindvall et al. (1992) *Ann. Neurol.* 31:155; and Lindvall et al. (1992) *Arch. Neurol.* 46:615). A preferred dosage range for immunosuppressive drugs, suitable for treatment of humans, is about 1–30 mg/kg of body weight per day. A preferred dosage range for cyclosporin A is about 1–10 mg/kg of body weight per day, more preferably about 1–5 mg/kg of body weight per day. Dosages can be adjusted to maintain an optimal level of the immunosuppressive drug in the serum of the recipient subject. For example, dosages can be adjusted to maintain a preferred serum level for cyclosporin A in a human subject of about 100–200 ng/ml. It is to be noted that dosage values may vary according to factors such as the disease state, age, sex, and weight of the individual. Dosage regimens may be adjusted over time to provide the optimum therapeutic response according to the individual need and the professional judgment of the person administering or supervising the administration of the compositions, and that the dosage ranges set forth herein are exemplary only and are not intended to limit the scope or practice of the claimed composition.

In one embodiment of the invention, an immunsuppressive drug is administered to a subject transiently for a sufficient time to induce tolerance to the transplanted cells in the subject. Transient administration of an immunosuppressive drug has been found to induce long-term graft-specific tolerance in a graft recipient (See Brunson et al. (1991) *Transplantation* 52:545; Hutchinson et al. (1981) *Transplantation* 32:210; Green et al. (1979) *Lancet* 2:123; Hall et al. (1985) *J. Exp. Med.* 162:1683). Administration of the drug to the subject can begin prior to transplantation of the cells into the subject. For example, initiation of drug administration can be a few days (e.g., one to three days) before transplantation. Alternatively, drug administration can begin the day of transplantation or a few days (generally not more than three days) after transplantation. Administration of the drug is continued for sufficient time to induce donor cell-specific tolerance in the recipient such that donor cells will continue to be accepted by the recipient when drug administration ceases. For example, the drug can be administered for as short as three days or as long as three months following transplantation. Typically, the drug is administered for at least one week but not more than one month following transplantation. Induction of tolerance to the transplanted cells in a subject is indicated by the continued acceptance of the transplanted cells after administration of the immunosuppressive drug has ceased. Acceptance of transplanted tissue can be determined morphologically (e.g., with skin grafts by examining the transplanted tissue or by biopsy) or by assessment of the functional activity of the graft.

Another type of agent which can be used to inhibit T cell activity in a subject is an antibody, or fragment or derivative thereof, which depletes or sequesters T cells in a recipient. Antibodies which are capable of depleting or sequestering T cells in vivo when administered to a subject are known in the art. Typically, these antibodies bind to an antigen on the surface of a T cell. Polyclonal antisera can be used, for example anti-lymphocyte serum. Alternatively, one or more monoclonal antibodies can be used. Preferred T cell-depleting antibodies include monoclonal antibodies which bind to CD2, CD3, CD4 or CD8 on the surface of T cells. Antibodies which bind to these antigens are known in the art and are commercially available (e.g., from American Type Culture Collection). A preferred monoclonal antibody for binding to CD3 on human T cells is OKT3 (ATCC CRL 8001). The binding of an antibody to surface antigens on a T cell can facilitate sequestration of T cells in a subject and/or destruction of T cells in a subject by endogenous mechanisms. Alternatively, a T cell-depleting antibody which binds to an antigen on a T cell surface can be conjugated to a toxin (e.g., ricin) or other cytotoxic molecule (e.g., a radioactive isotope) to facilitate destruction of T cells upon binding of the antibody to the T cells. See U.S. patent application Ser. No.: 08/220,724, filed Mar. 31, 1994, for further details concerning the generation of antibodies which can be used in the present invention.

Another type of antibody which can be used to inhibit T cell activity in a recipient subject is an antibody which inhibits T cell proliferation. For example, an antibody directed against a T cell growth factor, such as IL-2, or a T cell growth factor receptor, such as the IL-2 receptor, can inhibit proliferation of T cells (See e.g., DeSilva, D. R. et al. (1991) *J. Immunol.* 147:3261–3267). Accordingly, an IL-2 or an IL-2 receptor antibody can be administered to a recipient to inhibit rejection of a transplanted cell (see e.g. Wood et al. (1992) *Neuroscience* 49:410). Additionally, both an IL-2 and an IL-2 receptor antibody can be coadministered to inhibit T cell activity or can be administered with another antibody (e.g., which binds to a surface antigen on T cells).

An antibody which depletes, sequesters or inhibits T cells within a recipient can be administered at a dose and for an appropriate time to inhibit rejection of cells upon transplantation. Antibodies are preferably administered intravenously in a pharmaceutically acceptable carrier or diluent (e.g., a sterile saline solution). Antibody administration can begin prior to transplantation (e.g., one to five days prior to transplantation) and can continue on a daily basis after transplantation to achieve the desired effect (e.g., up to fourteen days after transplantation). A preferred dosage range for administration of an antibody to a human subject is about 0.1–0.3 mg/kg of body weight per day. Alternatively, a single high dose of antibody (e.g., a bolus at a dosage of about 10 mg/kg of body weight) can be administered to a human subject on the day of introduction of the pancreatic cells into the subject. The effectiveness of antibody treatment in depleting T cells from the peripheral blood can be determined by comparing T cell counts in blood samples taken from the subject before and after antibody treatment. Dosage regimes can be adjusted over time to provide the optimum therapeutic response according to the individual need and the professional judgment of the person administering or supervising the administration of the compositions. Dosage ranges set forth herein are exemplary only and are not intended to limit the scope or practice of the claimed composition.

To assess their therapeutic potential, the porcine pancreatic cells of the invention can be introduced into existing animal models for diabetes. These models include, for example, mice in which diabetes is induced by, for example, intravenous injection of alloxan (Korsgren, O. et al. (1993) *Surgery* 113:205–214) or administration of streptozocin (Liu, X. et al. (1991) *Diabetes* 858–866). Other animal models of diabetes include db/db and ob/ob mouse lines (Pittman et al. (1994) *Transplant. Proc.* 26:1135–1137). Therapeutic efficacy in these models of diabetes can be predictive of therapeutic efficacy in humans. Groth, C. G. et al. (1992) *Transplant. Proc.* 24(3):972–973. The therapeutic efficacy of the administered porcine pancreatic cells is typically determined by, for example, measurement of blood glucose concentrations using, for example, an intravenous glucose tolerance test, before and after administration of the porcine pancreatic cells. Normalization of hyperglycemia demonstrates that the administered porcine pancreatic cells can be used to treat diseases characterized by insufficient insulin secretion. Other methods of determining the therapeutic potential are histological examination of the pancreatic cell graft (via a biopsy), e.g., by staining for insulin, and measurement of insulin levels in blood by, for example, radioimmunoassay.

This invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLES

Example I

DISSECTION OF PANCREATIC CELLS FROM EMBRYONIC SWINE

Female pigs were inseminated 31–35 days prior to euthanization and removal of uterus. After uterus was surgically removed and transported to sterile laboratory facilities, fetuses were delivered into a sterile dish containing calcium-magnesium free phosphate buffered saline (PBS) in a horizontal laminar flow hood. Fetuses at this stage of development ranged from 25–45 mm in length (crown-to-rump length).

Fetuses were removed from the storage dish containing PBS and placed in a sterile dissecting dish containing PBS. The dissecting dish was then placed on the stage of a dissecting microscope. With the aid of the dissecting microscope, a longitudinal incision was made down the midline of the fetus. Next, an incision was made at right angles to the first incision just below the ribs and chest cavity. The overlying skin was pulled back to expose the internal organs of the fetus. The liver, which is the large red organ occupying virtually the entire ventral body cavity, was located and removed. After the liver was removed the stomach and small intestine were located. The stomach was white and kidney shaped at this stage of development. Once located, the stomach was followed to the point where it joins the small intestine. At the juncture between the stomach and the small intestine, the dorsal aspect of the fetal pancreas can be identified lying in close apposition to the stomach. The fetal pancreas was the same color as the stomach and difficult to locate. Once the pancreas had been located, it was observed that the pancreas is a small tongue-like structure that was U-shaped and surrounded the posterior half of the stomach. With the fetal pancreas located, it was dissected away from the stomach with a pair of forceps and microscissors then placed in a tube containing sterile PBS. The procedure was repeated for all fetuses from a single donor sow.

Figure 1B:
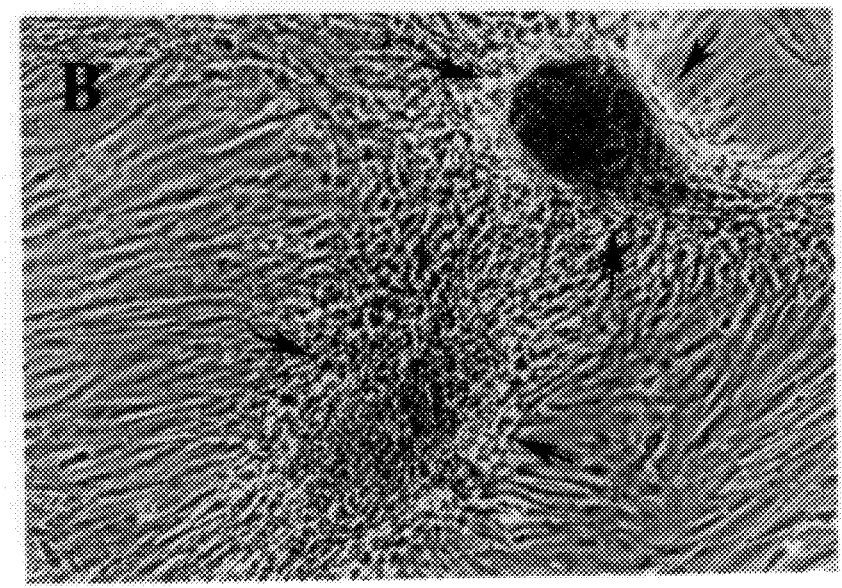

The PBS was removed from the tube containing dissected pancreases. The tissue was then resuspended in 1.5 ml of 0.05% Trypsin, 0.53 mM EDTA and incubated at 37° C. for 15 minutes. Tissue was dissociated by triturating with a pasteur pipette until a uniform cell suspension was formed. Trypsin was stopped by adding 5 ml of medium (RPMI-1640+10% FCS), then the cells were collected at 1000 RPM for 5 minutes at 25° C. Cells were resuspended in culture media (RPMI-1640+10% FCS+5 ng/ml PDGF+100 ng/ml EGF) and plated in sterile tissue culture dishes. Cells were then allowed to adhere and grow at 37° C. in an incubator with 5% $CO_2$. FIGS. 1A–1B depict insulin staining of the cultured fetal pig pancreatic cells. FIG. 1A is a phase micrograph of fetal pig pancreatic cells in monolayer prior to formation of islet-like clusters after two weeks of culture. No insulin staining can be detected in these cells at this time. FIG. 1B is a phase micrograph of fetal pig pancreatic cells after three weeks of culture that were allowed to form islet-like clusters (indicated by arrows). These cells stained positive for insulin.

The growth rate behavior of the pancreatic cells includes a doubling time of 80 hours without growth factors and 58 hours with growth factors. Fourteen fetuses provided approximately $1-2 \times 10^6$ pancreatic cells. The cells can be cultured for 30 days to yield $4-8 \times 10^9$ cells. The length of time required for islet-like aggregate or cluster formation is 4–7 days after the cells reach confluence.

Example II

INTRODUCTION OF PORCINE PANCREATIC CELLS INTO XENOGENEIC RECIPIENTS AND DEMONSTRATION OF INSULIN-SECRETION IN VIVO

Figure 2A:
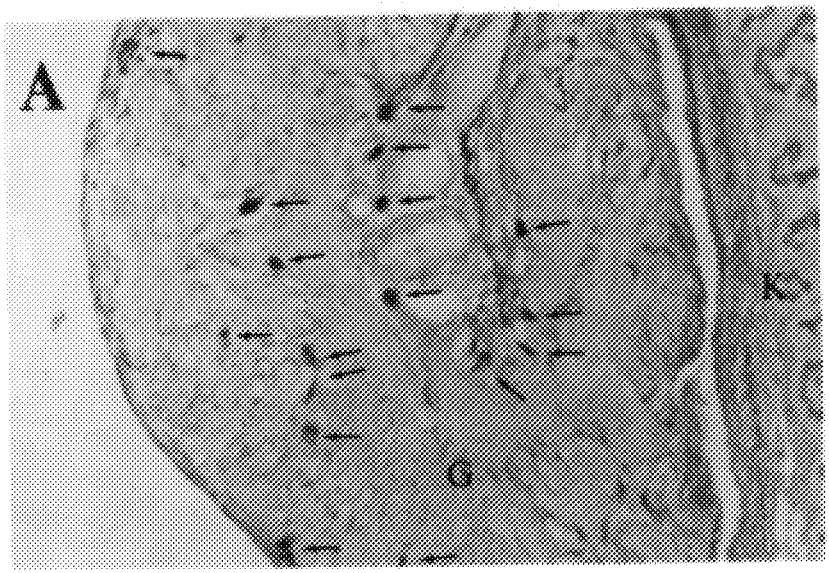
FIGS. 2A–2B depict grafts obtained from fetal pig pancreatic cells transplanted into nude mice.
Figure 2B:
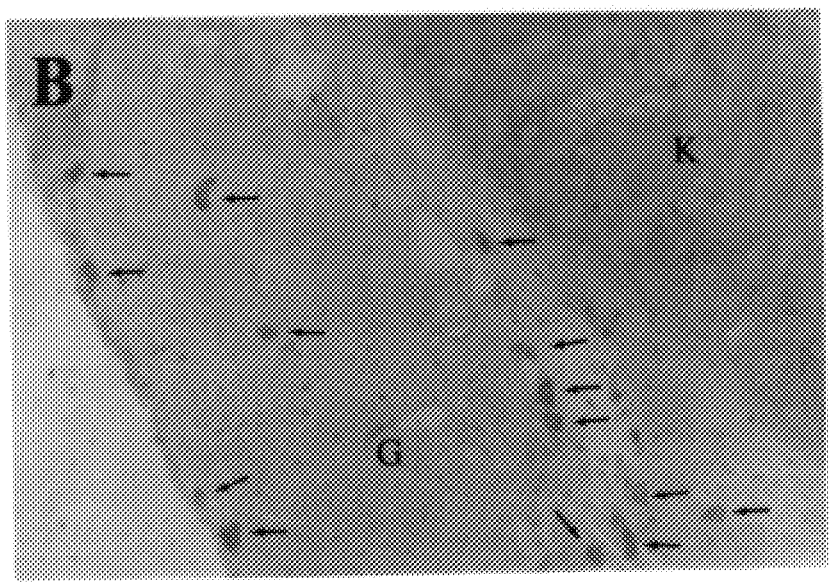

All transplantations were done into nude mice recipients. Mice were anaesthetized by intraperitoneal administration of Avertin (250 mg/kg body weight) and a flank incision was made to expose the kidney. A small incision was made on the kidney and a small fire polished glass rod was inserted between the kidney epithelium and the kidney tissue to create a space for cells to be transplanted. Prior to transplantation, $10^6$ proliferating cells (which did not stain for insulin) were either immobilized in a rat tail collagen matrix or in a blood clot. For immobilization in rat tail collagen, 8 parts collagen at 5.29 mg/ml+1 part 0.1M NaOH+1 part 10× Hank's balanced salt solution (HBSS) were combined and the pH was adjusted to 7.4 with 0.1M NaOH. Collagen was kept at 4° C. until addition to cells. Collagen did not readily gel at 4° C. or when pH was below 7.4, therefore, adjusting pH and warming to room temperature were essential for formation of a collagen gel. Immobilized cells were placed with forceps through the incision made on the kidney in the space previously created. The skin incision was then closed with a wound clip and the animal transferred to a cage for recovery. In the first experiments, 12 animals were transplanted: 6 animals received cells immobilized in collagen. At one month post-transplant, 3 animals from each group were sacrificed and the transplanted kidneys processed for histology and immunostaining. The remaining animals are sacrificed at 3 months post-transplantation. For the animals that were sacrificed, grafts were found in 5 or 6 animals: one animal inadvertently received 1/10 the number of cells intended and that was the animal with no graft. There was no apparent difference between grafts derived from cells immobilized in blood clots or collagen. All grafts stained positive for insulin. For example, FIG. 2A is a section from transplanted kidney showing the graft stained with aldehyde-fuchsin. Insulin-containing cells stain darkly and can be seen scattered throughout the graft. FIG. 2B shows insulin staining from the same graft which is stained with a primary Mouse Insulin Ab monoclonal (Chemicon Intl., Inc., Temecula, Calif.) and a secondary goat-anti-mouse antibody conjugated with horseradish peroxidase (Vector Labs Inc., Burlingame, Calif.). The insulin-containing cells within the graft stain more darkly than the other cells. In both figures, the insulin-positive cells are indicated by arrows, the donor graft is marked (G), and the recipient mouse kidney is marked (K).

Example III

METHODS OF PRODUCING ESSENTIALLY PATHOGEN-FREE SWINE FROM WHICH PANCREATIC CELLS OF THE INVENTION CAN BE OBTAINED

A. Collecting, processing, and analyzing pig fecal samples for signs of pathogens Feces are extracted from the pig's rectum manually and placed in a sterile container. About a 1.5 cm diameter portion of the specimen was mixed thoroughly in 10 ml of 0.85% saline. The mixture is then strained slowly through a wire mesh strainer into a 15 ml conical centrifuge tube and centrifuged at 650×g for 2 minutes to sediment the remaining fecal material. The supernatant is decanted carefully so as not to dislodge the sediment and 10% buffered formalin was added to the 9 ml mark, followed by thorough mixing. The mixture is allowed to stand for 5 minutes. 4 ml of ethyl acetate is added to the mixture and the mixture is capped and mixed vigorously in an inverted position for 30 seconds. The cap is then removed to allow for ventilation and then replaced. The mixture is centrifuged at 500×g for 1 minute (four layers should result: ethyl acetate, debris plug, formalin and sediment). The debris plug is rimmed using an applicator stick. The top three layers are carefully discarded by pouring them off into a solvent container. The debris attached to the sides of the tube is removed using a cotton applicator swab. The sediment is mixed in either a drop of formalin or the small amount of formalin which remains in the tube after decanting. Two separate drops are placed on a slide to which a drop of Lugol's iodine is added. Both drops are coverslipped and carefully examined for signs of pathogens, e.g., protozoan cysts of trophozoites, helminth eggs and larvae. Protozoan cyst identification is confirmed, when required, by trichrome staining.

B. Co-cultivation assay for detecting the presence of human and animal viruses in pig cells Materials

Cell Lines

African green monkey kidney, (VERO), cell line American Type Culture Collection, (ATCC CCL81), human embryonic lung fibroblasts, (MRC-5) cell line American Type Culture Collection, (ATCC CCL 171), porcine kidney, (PK-15), cell line American Type Culture Collection, (ATCC CRL 33), porcine fetal testis, (ST), cell line American Type Culture Collection, (ATCC CRL 1746).

Medium, Antibiotics, and Other Cells, and Equipment

Fetal calf serum, DMEM, Penicillin 10,000 units/ml, Streptomycin 10 mg/ml, Gentamicin 50 mg/ml, guinea pig erythrocytes, chicken erythrocytes, porcine erythrocytes, Negative Control (sterile cell culture medium), Positive Controls: VERO and MRC-5 Cells: Poliovirus type 1 attenuated, (ATCC VR-1 92) and Measles virus, Edmonston strain, (ATCC VR-24), PK-1 5 and ST Cells: Swine influenza type A, (ATCC VR-99), Porcine Parvovirus, (ATCC VR-742), and Transmissible gastroenteritis of swine, (ATCC VR-743). Equipment: tissue Culture Incubator, Inverted Microscope, Biological Safety Cabinet.

These materials can be used in a co-cultivation assay (a process whereby a test article is inoculated into cell lines (VERO, MRC-5, PK1 5, and ST) capable of detecting a broad range of human, porcine and other animal viruses). Hsuing, G. D., "Points to Consider in the Characterization of Cell Lines Used to Produce Biologicals" in Diagnostic Virology, 1982 (Yale University Press, New Haven, Conn., 1982).

Experimental Design and Methodology

A total of three flasks (T25) of each cell line are inoculated with at least 1 ml of test article. Three flasks of each cell line can also be inoculated with the appropriate sterile cell culture medium as a negative control. Positive control viruses are inoculated into three flasks of each cell line. After an absorption period, the inoculate is removed and all flasks incubated at 35°–37° C. for 21 days. All flasks are observed at least three times per week for the development of cytopathic effects, (CPE), of viral origin. Harvests are made from any flasks inoculated with the test article that show viral CPE.

At Day 7 an aliquot of supernatant and cells from the flasks of each test article are collected and at least 1 ml is inoculated into each of three new flasks of each cell line. These subcultures are incubated at 35°–37° C. for at least 14 days. All flasks are observed and tested as described above.

At Day 7, the flasks from each test article are also tested for viral hemadsorption, (HAd), using guinea pig, monkey and chicken erythrocytes at 2°–8° C. and 35°–37° C. at 14 days postinoculation.

At Day 21, if no CPE is noted, an aliquot of supernatant from each flask is collected, pooled, and tested for viral hemagglutination, (HA), using guinea pig, monkey, and chicken erythrocytes at 2°–8° C. and 35°–37° C. Viral identification is based on characteristic viral cytopathic effects (CPE) and reactivity in HA testing.

The test samples are observed for viral cytopathic effects in the following manner: All cultures are observed for viral CPE at least three times each week for a minimum of 21 days incubation. Cultures are removed from the incubator and observed using an inverted microscope using at least 40× magnification. 100× or 200× magnification is used as appropriate. If any abnormalities in the cell monolayers, including viral CPE, are noted or any test articles cause total destruction of the cell monolayer, supernatant and cells are collected from the flasks and samples are subcultured in additional flasks of the same cell line. Samples can be stored at −60° to −80° C. until subcultured. After 7 and 14 days incubation, two blind passages are made of each test article by collecting supernatant and cells from all flasks inoculated with each sample. Samples can be stored at −60° to −80° C. until subcultured.

Hemadsorbing viruses are detected by the following procedure: after 21 days of incubation, a hemadsorption test is performed on the cells to detect the presence of hemadsorbing viruses. The cells are washed 1–2 times with approximately 5 mls of PBS. One to two mls of the appropriate erythrocyte suspension (either guinea pig, porcine, or chicken erythrocytes), prepared as described below, is then added to each flask. The flasks are then incubated at 2°–8° C. for 15–20 minutes, after which time the unabsorbed erythrocytes are removed by shaking the flasks. The erythrocytes are observed by placing the flasks on the lowered stage of a lab microscope and viewing them under low power magnification. A negative result is indicated by a lack of erythrocytes adhering to the cell monolayer. A positive result is indicated by the adsorption of the erythrocytes to the cell monolayer.

Hemagglutination testing, described in detail below, is also performed after 21 days of incubation of the subcultures. Viral isolates are identified based on the cell line where growth was noted, the characteristics of the viral CPE, the hemadsorption reaction, and hemagglutination reactions, as appropriate. The test article is considered negative for the presence of a viral agent, if any of the cell lines used in the study demonstrate viral, CPE, HA, or HAd in a valid assay.

C. Procedure for preparing and maintaining cell lines used to detect viruses in pig cells Materials Fetal calf serum (FCS), DMEM, Penicillin 10,000 unit/ml, Streptomycin 10 mg/ml, Gentamicin 50 mg/ml, T25 tissue culture flasks, tissue culture incubator (5% $CO_2$, 37° C.).

Procedure

Aseptic techniques are followed when performing inoculations and transfers. All inoculations and transfers are performed in a biological safety cabinet. Media is prepared by adding 10% FCS for initial seeding, 5% FCS for maintenance of cultures, as well as 5.0 ml of penicillin/streptomycin and 0.5 ml of gentamicin per 500 ml media. Sufficient media is added to cover the bottom of a T25 tissue culture flask. The flask is seeded with the desired cell line and incubated at 37° C., 5% $CO_2$ until cells are 80 to 100% confluent. The flasks are then inoculated with virus (QCP25).

D. Preparation of erythrocyte (rbc) suspensions used in hemadsorption (HAd) and hemagglutination (HA) virus detection testing Materials Phosphate buffered saline, (PBS), pH 7.2, guinea pig erythrocytes stock solution, porcine erythrocytes stock solution, chicken erythrocytes stock solution, sterile, disposable centrifuge tubes, 15 or 50 ml Laboratory centrifuge.

Procedure

An appropriate amount of erythrocytes (rbc) is obtained from stock solution. The erythrocytes are washed 3 times with PBS by centrifugation at approximately 1000×g for 10 minutes. A 10% suspension is prepared by adding 9 parts of PBS to each one part of packed erythrocytes. The 10% rcb suspensions are stored at 2°–8° C. for no more than one week. 0.5% ecb suspensions are prepared by adding 19 parts of PBS to each one part of 10% rbc suspension. Fresh 0 5% rbc suspensions are prepared prior to each day's testing.

Hemagglutination (HA) Test

A hemagglutination test is a test that detects viruses with the property to agglutinate erythrocytes, such as swine influenza type A, parainfluenza, and encephalomyocarditus viruses, in the test article. Hsuing, G. D. (1982) Diagnostic Virology (Yale University Press, New Haven, Conn.); Stites, Daniel P. and Terr, Abba I., (1991), Basic and Clinical Immunology (Appleton & Lange, East Norwalk, Conn.).

Materials

Supernatants from flasks of the VERO cell line, MRC-5 inoculated with the test article, flasks of positive and negative controls, phosphate buffered saline (PBS), pH 7.2, guinea pig erythrocytes (GPRBC), 0.5% suspension in PBS, chicken erythrocytes (CRBC), 0.5% suspension in PBS, porcine erythrocytes (MRBC), 0.5% suspension in PBS.

Procedure

All sample collection and testing is performed in an approved biological safety cabinet. 0.5% suspensions of each type of erythrocytes are prepared as described above. The HA test on all cell lines inoculated with samples of the test articles at least 14 days post-inoculation. Positive and negative control cultures are included for each sample and monolayers are examined to ensure that they are intact prior to collecting samples.

At least 1 ml of culture fluid from each flask inoculated with the test article is collected and pooled. 1 ml samples from the negative and positive control cultures are also collected and pooled. A set of tubes is labeled with the sample number and type of erythrocyte (distinguish positive and negative suspension) to be added. Racks may be labeled to differentiate the type of erythrocyte. 0.1 ml of sample is added to each tube. 0.1 ml of the appropriate erythrocyte suspension is added to each tube. Each tube is covered with parafilm and mixed thoroughly. One set of tubes is incubated at 2°–8° C. until tight buttons form in the negative control in about 30–60 minutes. Another set of tubes is incubated at 35°–37° C. until tight buttons form in the negative control in about 30–60 minutes.

Formation of a tight button of erythrocytes indicates a negative result. A coating of the bottom of the tube with the erythrocytes indicates a positive result.

E. Methods used for fluorescent antibody stain of cell suspensions obtained from flasks used in detection of viruses in porcine cells using cell culture techniques (as described in Sections B and C)

Materials

Pseudorabies, parvovirus, enterovirus, adenovirus, transmissible Gastroenteritis Virus, bovine viral diarrhea, encephalomyocarditus virus, parainfluenza, vesicular stomatitis virus, microscope slides, PBS, incubator with humidifying chamber at 36° C., Evan's blue coutner stain, DI Water, fluorescent microscope, trypsin, serum containing media, acetone, T25 Flask.

Procedure

Cells (described in Sections B and C) are trypsinized to detach them from the T25 flask and sufficient media is added to neutralize trypsin activity. A drop of cell suspension is placed on each microscope slide and allowed to air dry. A slide for each fluorescent antibody is prepared. Cells are fixed by immersion in acetone for five minutes. Each fluorescent antibody solution is placed on each slide to cover cells and the slides are incubated in humidifying chamber in incubator at 36° C. for 30 minutes. The slides are then washed in PBS for five minutes. The wash is repeated in fresh PBS for five minutes followed by a rinse with DI water.

The cells are counterstained by placing Evan's blue solution on each slide to cover cells for five minutes at room temperature. The slides are then washed in PBS for five minutes. The wash is repeated in fresh PBS for five minutes followed by a rinse with DI water. The slides are then allowed to air dry. Each slide is inspected under a fluorescent microscope. Any fluorescent inclusion bodies characteristic of infection are considered a positive result for the presence of virus.

F. Procedures for Defining Bacteremic Pigs

Materials

Anaerobic BMB agar (5% sheep blood, vitamin K and hemin [BMB/blood]), chocolate Agar with Iso Vitalex, Sabaroud dextrose agar/Emmons, 70% isopropyl alcohol swabs, betadine solution, 5% $CO_2$ incubator at 35°–37° C., anaerobic blood agar plate, gram stain reagents (Columbia Broth Media), aerobic blood culture media (anaerobic brain heart infusion with vitamin K & hemin), septicheck media system, vitek bacterial identification system, laminar flow hood, microscope, and bacteroids and Bacillus stocks.

Procedure

Under a laminar flow hood, disinfect the tops of bottles for aerobic and anaerobic blood cultures of blood obtained from pig with 70% isopropyl alcohol, then with betadine. The rubber stopper and cap from the aerobic blood culture bottle are removed and a renal septicheck media system is attached to the bottle. The bottles are incubated in 5% $CO_2$ for 21 days at 35°–37° C., and observed daily for any signs of bacterial growth (i.e. gas bubbles, turbidity, discoloration or discrete clumps). Negative controls consisting of 5 cc of sterile saline in each bottle and positive controls consisting of *Bacillus subtilis* in the aerobic bottle and *Bacteriodes Vulgaris* in the anaerobic bottle are used. If signs of bacterial growth are observed, a Gram stain is prepared and viewed microscopically at 100× oil immersion for the presence of any bacteria or fungi. The positive bottles are then subcultured onto both chocolate agar plates with Iso Vitlex and onto BMB plates. The chocolate plate is incubated at 35°–37° C. in 5% $CO_2$ for 24 hours and the BMB anaerobically at 35°–37° C. for 48 hours. Any yeast or fungi that is in evidence at gram stain is subcultured onto a Sabaroud dextrose/Emmons plate. The Vitek automated system is used to identify bacteria and yeast. Fungi are identified via their macroscopic and microscopic characteristic. If no signs of growth are observed at the end of 21 days, gram stain is prepared and observed microscopically for the presence of bacteria and fungi.

Absence of growth in the negative control bottles and presence of growth in the positive control bottles indicates a valid test. The absence of any signs of growth in both the aerobic and anaerobic blood culture bottles, as well as no organisms seen on gram stain indicates a negative blood culture. The presence and identification of microorganism(s) in either the aerobic or anaerobic blood culture bottle indicates of a positive blood culture; this typicall is due to a bacteremic state.

Equivalents

Those skilled in the art will recognize, or be able to ascertain using no more than routine experimentation. many equivalents of the specific embodiments of the invention described herein. Such equivalents are intended to be encompassed by the following claims.

I claim:

1. A method of treating a disease characterized by insufficient insulin activity in a subject, comprising administering to the subject an isolated population of porcine pancreatic cells, which cells, in unmodified form, have at least one antigen on the surface of the cells which is capable of stimulating an immune response against the cells in a xenogeneic subject, wherein the antigen on the surface of the cells is altered to inhibit rejection of the cells when administered to the subject.

2. The method of claim 1, wherein the porcine pancreatic cells are in the form of islet-like aggregates.

3. The method of claim 1, wherein the antigen on the surface of the cells which is altered is an MHC class I antigen.

4. The method of claim 3, wherein the cells are contacted prior to introduction into a xenogeneic subject with at least one MHC class I antibody, or fragment or derivative thereof, which binds to the MHC class I antigen on the surface of the cells but does not activate complement or induce lysis of the cells.

5. The method of claim 4, wherein the MHC class I antibody is an anti-MHC class I $F(ab')_2$ fragment.

6. The method of claim 5, wherein the MHC class I $F(ab')_2$ fragment is a $F(ab')_2$ fragment of a monoclonal antibody PT85.

7. The method of claim 1, wherein the cells in the population are obtained from an embryonic pig.

8. The method of claim 7, wherein the embryonic pig is between about day 31 and about day 35 of gestation.

9. The method of claim 1, wherein the pig from which the pancreatic cells are isolated is essentially free from at least one organism or substance which is capable of transmitting infection or disease to a xenogeneic recipient of the cells.

10. The method of claim 1, wherein the xenogeneic recipient is a human.

11. The method of claim 1, wherein the subject is a human and the disease is Type II diabetes.

12. A method of treating a disease characterized by insufficient insulin activity in a subject, comprising administering to a subject having the disease an isolated population of porcine pancreatic cells obtained from an embryonic pig which is essentially free from organisms and substances which are capable of transmitting infection or disease to a xenogeneic recipient of the cells, the embryonic pig being between about day 31 and about day 35 of gestation.

13. The method of claim 12, wherein the porcine pancreatic cells are obtained from a pig which is essentially free from at least one organism selected from the group consisting of parasites, bacteria, mycoplasma, and viruses.

14. The method of claim 12, wherein the porcine pancreatic cells are in the form of islet-like aggregates.

15. The method of claim 12, wherein the pig from which the pancreatic cells are isolated is essentially free from at least one zoonotic organism.

16. The method of claim 15, wherein the pig from which the pancreatic cells are isolated is further essentially free from at least one neurotropic organism.

17. The method of claim 16, wherein the neurotropic organism is selected from the group consisting of parasites, bacteria, and viruses.

18. The method of claim 17, wherein the parasites include toxoplasma.

19. The method of claim 17, wherein the bacteria include listeria.

20. The method of claim 17, wherein the viruses are selected from the group consisting of adenovirus, encephalomyocarditis virus, hemagglutinating encephalomyocarditis, parvovirus, pseudorabies virus, rabies virus, swine vesicular virus, and swine poliovirus.

21. The method of claim 15, wherein the zoonotic organism is selected from the group consisting of parasites, bacteria, and viruses.

22. The method of claim 21, wherein the viruses are selected from the group consisting of encephalomyocarditis virus, pseudorabies virus, rabies virus, swine influenza type A virus, transmissible gastroenteritis virus, and vesicular stomatitis virus.

23. The method of claim 15, wherein the pig from which the pancreatic cells are isolated is further essentially free from at least one cross-placental organism.

24. The method of claim 23, wherein the cross-placental organism is selected from the group consisting of parasites, bacteria, mycoplasm, and viruses.

25. The method of claim 24, wherein the parasites are selected from the group consisting of eperythrozoon and toxoplasma.

26. The method of claim 24, wherein the bacteria are selected from the group consisting of brucella, leptospirillum, and listeria.

27. The method of claim 24, wherein the mycoplasm includes mycoplasma hyopneunomia.

28. The method of claim 24, wherein the viruses are selected from the group consisting of hemagglutinating encephalomyocarditis virus, parvovirus, pseudorabies virus, porcine respiratory reproductive system virus, rabies virus, suipoxvirus, swine influenza type A virus, swine vesicular disease virus, and swine poliovirus.

29. The method of claim 23, wherein the pig from which the pancreatic cells are isolated is further essentially free from at least one neurotropic organism.

30. The method of claim 12, wherein the pig from which the pancreatic cells are isolated is essentially free from at least one cross-placental organism.

31. The method of claim 30, wherein the pig from which the neural cell is isolated is further essentially free from at least one neurotropic organism.

32. The method of claim 31, wherein the parasites include toxoplasma.

33. The method of claim 31, wherein the bacteria are selected from the group consisting of brucella, listeria, mycobacterium TB, and leptospirillum.

34. The method of claim 12, wherein xenogeneic recipient is a human.

35. The method of claim 12, wherein the subject is a human and the disease is Type II diabetes.

* * * * *